US00PP32555P2

(12) United States Plant Patent
Vlielander

(10) Patent No.: US PP32,555 P2
(45) Date of Patent: Dec. 1, 2020

(54) ***KALANCHOE* PLANT NAMED 'DOKALGLOSS'**

(50) Latin Name: *Kalanchoe blossfeldiana*
Varietal Denomination: Dokalgloss

(71) Applicant: DUMMEN GROUP B.V., De Lier (NL)

(72) Inventor: Ike Vlielander, De Lier (NL)

(73) Assignee: Dümmen Group B.V., DeLier (NL)

( * ) Notice: Subject to any disclaimer, the term of this patent is extended or adjusted under 35 U.S.C. 154(b) by 0 days.

(21) Appl. No.: 16/602,996

(22) Filed: Jan. 13, 2020

(30) Foreign Application Priority Data

Nov. 14, 2019 (QZ) ..... PBR 2019/2994

(51) Int. Cl.
*A01H 5/02* (2018.01)
*A01H 6/32* (2018.01)

(52) U.S. Cl.
USPC ..... Plt./335

(58) Field of Classification Search
USPC ..... Plt./335
CPC ... A01H 5/02; A01H 5/00; A01H 6/32; A01H 6/324
See application file for complete search history.

*Primary Examiner* — June Hwu
(74) *Attorney, Agent, or Firm* — C. A. Whealy

(57) ABSTRACT

A new and distinct cultivar of *Kalanchoe* plant named 'Dokalgloss', characterized by its relatively compact, upright and uniformly mounded plant habit; moderately vigorous growth habit; freely branching plant habit; glossy dark green-colored leaves; uniform, early and freely flowering habit; large red purple and light red purple bi-colored flowers; and excellent postproduction longevity.

2 Drawing Sheets

Figure 1:
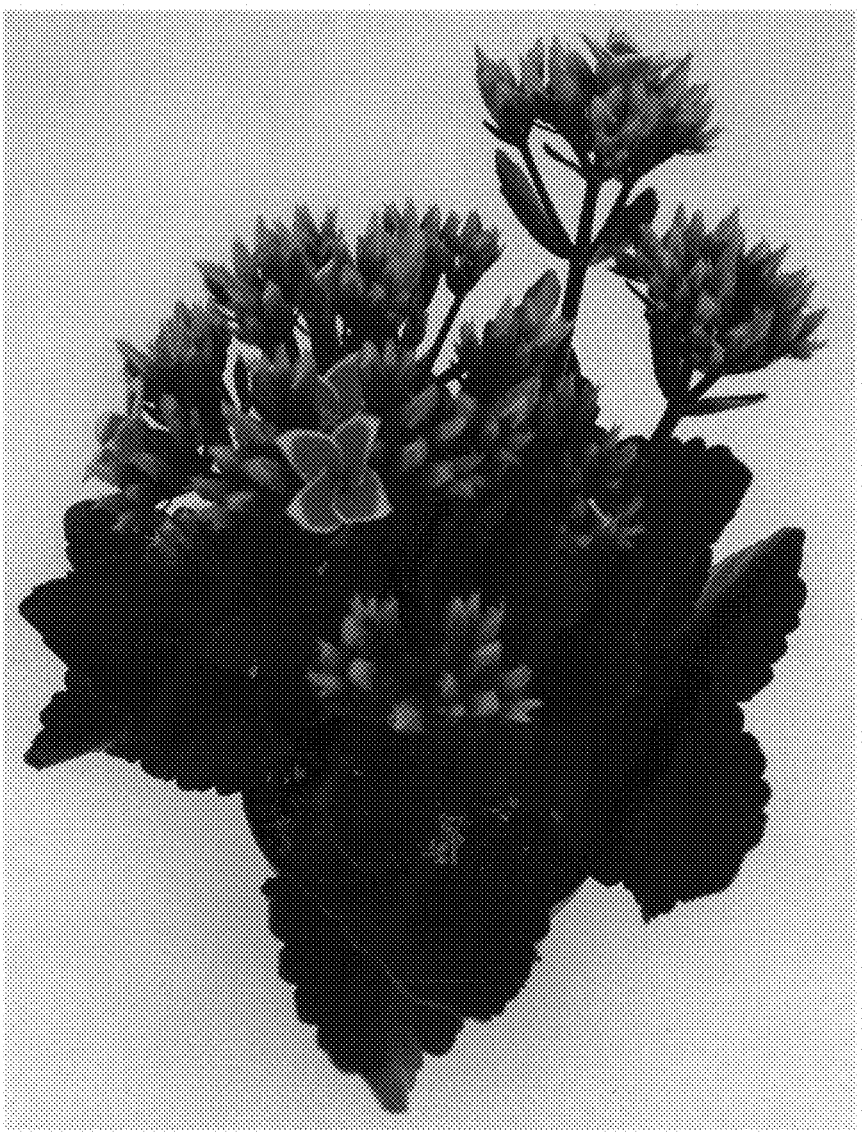

Botanical designation: *Kalanchoe blossfeldiana.*
Cultivar denomination: 'DOKALGLOSS'.

BACKGROUND OF THE INVENTION

The present invention relates to a new and distinct *Kalanchoe* plant, botanically known as *Kalanchoe blossfeldiana* and hereinafter referred to by the name 'Dokalgloss'.

The new *Kalanchoe* is a product of a planned breeding program conducted by the Inventor in De Lier, The Netherlands. The objective of the breeding program is to create new freely-branching and freely-flowering *Kalanchoe* plants with attractive leaf and flower coloration.

The new *Kalanchoe* plant originated from a cross-pollination made by the Inventor in De Lier, The Netherlands in April, 2014 of a proprietary selection of *Kalanchoe blossfeldiana* identified as code number 082242-02, not patented, as the female, or seed, parent with a proprietary selection of *Kalanchoe blossfeldiana* identified as code number 5353-01, not patented, as the male, or pollen, parent. The new *Kalanchoe* plant was discovered and selected by the Inventor as a single flowering plant from within the progeny of the stated cross-pollination in a controlled environment in De Lier, The Netherlands in March, 2015.

Asexual reproduction of the new *Kalanchoe* plant by vegetative terminal cuttings in a controlled environment in De Lier, The Netherlands since 2015 has shown that the unique features of this new *Kalanchoe* plant are stable and reproduced true to type in successive generations.

SUMMARY OF THE INVENTION

Plants of the new *Kalanchoe* have not been observed under all possible combinations of environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Dokalgloss'. These characteristics in combination distinguish 'Dokalgloss' as a new and distinct *Kalanchoe* plant:

1. Relatively compact, upright and uniformly mounded plant habit.
2. Moderately vigorous growth habit.
3. Freely branching plant habit.
4. Glossy dark green-colored leaves.
5. Uniform, early and freely flowering habit.
6. Large red purple and light red purple bi-colored flowers.
7. Excellent postproduction longevity.

Plants of the new *Kalanchoe* can be compared to plants of the female parent selection. Plants of the new *Kalanchoe* differ from plants of the female parent selection in the following characteristics:

1. Plants of the new *Kalanchoe* are larger and more vigorous than plants of the female parent selection.
2. Plants of the new *Kalanchoe* are more freely branching than plants of the female parent selection.
3. Flowers of plants of the new *Kalanchoe* are slightly smaller than flowers of plants of the female parent selection.

Plants of the new *Kalanchoe* can be compared to plants of the male parent selection. Plants of the new *Kalanchoe* differ from plants of the male parent selection in the following characteristics:

1. Plants of the new *Kalanchoe* are larger than plants of the male parent selection.
2. Flowers of plants of the new *Kalanchoe* are larger than flowers of plants of the male parent selection.

3. Plants of the new *Kalanchoe* and the male parent selection differ in flower color as plants of the new *Kalanchoe* have red purple and light red purple bicolored flowers whereas plants of the male parent selection have red-colored flowers.

Plants of the new *Kalanchoe* can be compared to plants of the *Kalanchoe blossfeldiana* 'Fikalpitonpi', disclosed in U.S. Plant Pat. No. 27,911. In side-by-side comparisons, plants of the new *Kalanchoe* differ primarily from plants of 'Fikalpitonpi' in the following characteristics:

1. Plants of the new *Kalanchoe* are more freely branching than plants of 'Fikalpitonpi'.
2. Plants of the new *Kalanchoe* flower earlier than plants of 'Fikalpitonpi'.
3. Plants of the new *Kalanchoe* have slightly larger flowers than plants of 'Fikalpitonpi'.
4. Plants of the new *Kalanchoe* and 'Fikalpitonpi' differ in flower color as flowers of plants of 'Fikalpitonpi' are lighter in color than flowers of the new *Kalanchoe*.

BRIEF DESCRIPTION OF THE PHOTOGRAPHS

The accompanying colored photographs illustrate the overall appearance of the new *Kalanchoe* plant showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet (FIG. 1 of 2) is a side perspective view of a typical flowering plant of 'Dokalgloss' grown in a container.

Figure 2:
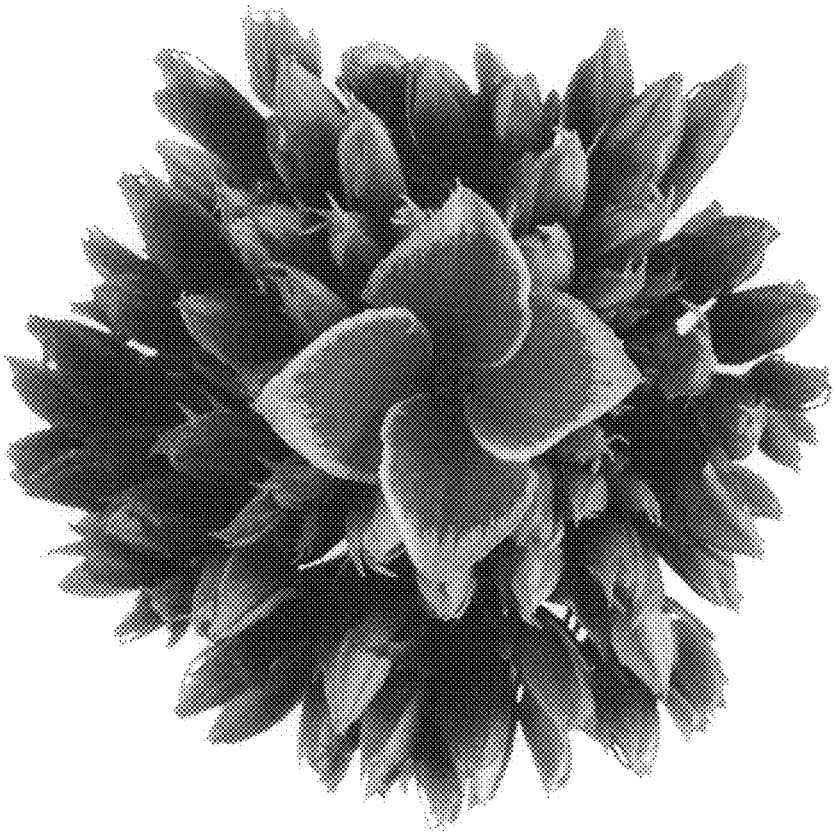

The photograph on the second sheet (FIG. 2 of 2) is a close-up view of a typical open flower and flower buds of 'Dokalgloss'.

DETAILED BOTANICAL DESCRIPTION

The aforementioned photographs and following observations, measurements and values describe plants grown during the autumn in 10-cm containers in a glass-covered greenhouse in De Lier, The Netherlands and under cultural practices typical of commercial *Kalanchoe* production. During the production of the plants, day temperatures ranged from 18° C. to 20° C., night temperatures averaged 18° C. and light levels ranged from 10,000 lux to 50,000 lux. Plants received long day/short night conditions (more than 14 hours of light) for three weeks then plants received photoinductive short day/long night conditions (minimum 14 hours darkness) until flowering. Plants were eleven weeks old when the photographs were taken and twelve weeks old when the description was taken. In the detailed description, color references are made to The Royal Horticultural Society Colour Chart, 2007 Edition, except where general terms of ordinary dictionary significance are used.

Botanical classification: *Kalanchoe blossfeldiana* 'Dokalgloss'.

Parentage:

*Female, or seed, parent*.—Proprietary selection of *Kalanchoe blossfeldiana* identified as code number 082242-02, not patented.

*Male or pollen parent*.—Proprietary selection of *Kalanchoe blossfeldiana* identified as code number 5353-01, not patented.

Propagation:

*Type*.—By vegetative terminal cuttings.

*Time to initiate roots, summer*.—About twelve days at temperatures about 21° C.

*Time to initiate roots, winter*.—About 15 days at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Fine, fibrous; typically greyish white to reddish brown in color, actual color of the roots is dependent on substrate composition, water quality, fertilizer type and formulation, substrate temperature and physiological age of roots.

*Rooting habit*.—Moderately freely branching; medium density to sparse.

Plant description:

*Plant and growth habit*.—Relatively compact, upright and uniformly mounded plant habit; freely flowering habit with numerous cymes positioned above the foliar plane; triangular in shape with rounded crown; appropriate for 5 to 10-cm containers; moderately vigorous growth habit; moderate growth rate.

*Plant height at flowering*.—About 16 cm.

*Plant diameter at flowering*.—About 15 cm.

*Branching habit*.—Freely branching habit with about five to seven lateral branches developing per plant; pinching (removal of the terminal apex) is not required but will enhance lateral branch development.

Lateral branch description:

*Length*.—About 9 cm to 14 cm.

*Diameter*.—About 2 mm to 5 mm.

*Internode length*.—About 3 cm to 5 cm.

*Aspect*.—Mostly upright.

*Strength*.—Moderately strong.

*Texture and luster*.—Smooth, glabrous; semi-glossy.

*Color, developing and developed*.—Close to 147A.

Leaf description:

*Arrangement*.—Opposite, simple; generally symmetrical.

*Length*.—About 11 cm.

*Width*.—About 6.5 cm.

*Shape*.—Ovate to elliptic.

*Apex*.—Obtuse.

*Base*.—Obtuse.

*Margin*.—Vaulted.

*Texture and luster, upper surface*.—Smooth, glabrous; coriaceous; succulent; glossy.

*Texture and luster, lower surface*.—Smooth, glabrous; coriaceous; succulent; matte.

*Venation pattern*.—Pinnate.

*Color*.—Developing and fully developed leaves, upper surface: Close to 147A; venation, close to 147A. Developing and fully developed leaves, lower surface: Close to 147B; venation, close to 147B.

*Petioles*.—Length: About 1.2 cm. Diameter: About 4 mm to 7 mm. Strength: Moderately strong. Texture and luster, upper and lower surfaces: Smooth, glabrous; coriaceous; succulent; glossy. Color, upper surface: Close to 147A. Color, lower surface: Close to 147B.

Flower description:

*Flower arrangement and habit*.—Single-type flowers arranged in axillary cymes; uniform and freely flowering habit with usually more than 20 open flowers and more than 20 flower buds per lateral branch and more than 100 open flowers and flower buds developing per plant; plants flower continuously for at least seven weeks; flowers face mostly upright to outwardly depending on the position in the inflorescence.

*Fragrance*.—None detected.

*Natural flowering season*.—Plants of the new *Kalanchoe* initiate and develop flowers under short day/long night conditions or during November and December in the Northern Hemisphere; flower initiation and development can also be induced under artificial short day/long conditions (at least 14 hours of darkness).

*Time to flower*.—Early flowering habit, under short day/long night photoinductive conditions, plants begin flowering about nine to eleven weeks; actual time to flower is primarily dependent upon temperature and light intensity.

*Post-production longevity*.—Excellent post-production longevity; plants maintain good foliage and flower substance for about 58 days under interior conditions; individual flowers last about 23 days on the plant; flowers persistent.

*Flower diameter*.—About 1.9 cm.

*Flower length* (*height*).—About 2.5 cm.

*Flower buds*.—Length: About 9 mm. Diameter: About 4 mm. Shape: Ovoid. Texture and luster: Smooth, glabrous; glossy. Color: Close to 138B.

*Petals*.—Arrangement: Four in a single whorl. Length: About 1.1 cm. Width: About 1 cm. Aspect: Somewhat upright. Shape: Ovate. Apex: Acute. Base: Obtuse. Margin: Entire. Texture and luster, upper and lower surfaces: Smooth, glabrous; slightly glossy. Color: When opening and fully opened, upper surface: Proximally, close to N57A; towards the margins, close to 68D; venation, similar to lamina colors; color does not change with development. When opening and fully opened, lower surface: Proximally, close to N57A; towards the margins, close to 63D; venation, similar to lamina colors; color does not change with development.

*Sepals*.—Appearance: Four in a single whorl. Length: About 1.3 cm. Width: About 3.5 mm. Shape: Oblong, pointed. Apex: Acute. Base: Obtuse. Margin: Entire. Aspect: Upright, rigid. Texture and luster, upper and lower surfaces: Smooth; glabrous; slightly glossy. Color, upper and lower surfaces: Close to 138B.

*Peduncles*.—Length: About 3 mm to 5 mm. Diameter: About 2 mm. Aspect: Erect, rigid. Strength: Moderately strong. Texture: Smooth, glabrous. Color: Close to 138B.

*Reproductive organs*.—Androecium: Stamen number: If present, about eight per flower. Filament length: About 3 mm. Filament color: Close to 155C. Anther size: About 0.1 mm by 0.3 mm. Anther shape: Elliptic, flat. Anther color: Close to 150D. Amount of pollen: Scarce. Pollen color: Close to 12A. Gynoecium: Pistil number: About four. Pistil length: About 8 mm. Style length: About 7 mm. Style color: Close to 138D. Stigma shape: Flat. Stigma color: Close to 8D, crystalline. Ovary color: Close to 138D.

*Seeds*.—Quantity per flower: If developed, up to 30 seeds per flower. Length: About 0.1 mm. Diameter: About 0.05 mm. Texture: Rough. Color: Close to 166C.

Temperature tolerance: Plants of the new *Kalanchoe* have been observed to tolerate temperatures from about 16° C. to about 35° C.

Pathogen & pest resistance: To date, plants of the new *Kalanchoe* have not been observed to be resistant to pathogens and pests common to *Kalanchoe* plants.

It is claimed:

1. A new and distinct *Kalanchoe* plant named 'Dokalgloss' as illustrated and described.

* * * * *